(12) United States Patent
Kasahara

(10) Patent No.: US 6,238,911 B1
(45) Date of Patent: May 29, 2001

(54) CULTURE VESSEL AND MICROSCOPE FOR OBSERVING SAMPLE IN CULTURE VESSEL

(75) Inventor: Takashi Kasahara, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/340,019

(22) Filed: Jun. 28, 1999

(30) Foreign Application Priority Data

Jun. 29, 1998 (JP) .................................................. 10-182547

(51) Int. Cl.[7] .................................................. C12M 1/20
(52) U.S. Cl. .................................. 435/288.4; 435/288.7; 435/305.3; 359/398; 356/246; 422/102
(58) Field of Search .............................. 435/287.1, 288.4, 435/288.7, 305.2, 305.3; 359/398; 356/246; 250/328; 422/102

(56) References Cited

U.S. PATENT DOCUMENTS

| | | |
|---|---|---|
| 3,843,231 | * 10/1974 | Borel et al. . |
| 4,004,150 | * 1/1977 | Natelson . |
| 4,465,938 | * 8/1984 | Kato et al. . |
| 4,601,545 | * 7/1986 | Kern . |
| 4,684,250 | * 8/1987 | Kukka et al. . |
| 4,690,900 | * 9/1987 | Kimmo et al. . |
| 4,722,598 | * 2/1988 | Ford . |

FOREIGN PATENT DOCUMENTS

| | | |
|---|---|---|
| 1234114 | * 11/1999 | (CN) . |
| 5-181068 | 7/1993 | (JP) . |
| 8-5929 | 1/1996 | (JP) . |
| 9-72843 | 3/1997 | (JP) . |

* cited by examiner

Primary Examiner—William H. Beisner
(74) Attorney, Agent, or Firm—Pillsbury Winthrop LLP

(57) ABSTRACT

The present invention provides a culture vessel and microscope that allows a wide area of favorable observation of the sample in the plural wells even when a negative refractive power is generated in the culture medium, wherein a ring-shaped opening, a condenser lens, a lens array, a well plate, an objective lens and a phase contrast plate are disposed in this order viewed from the light source side with a construction to place a phase contrast film of the phase contrast plate in a conjugated relation to the projection pupil position or projection pupil of the objective lens, and the culture vessel is constructed of the lens array and well plate with a relative disposition in which the optical axis of each lens is coaxial with the center line of the confronting each well; the aperture of the ring-shaped opening being smaller than the aperture of the ring-shaped opening that is used when the culture vessel is not disposed in the optical path.

5 Claims, 3 Drawing Sheets

CULTURE VESSEL AND MICROSCOPE FOR OBSERVING SAMPLE IN CULTURE VESSEL

BACKGROUND OF THE INVENTION

1. Field of the Invention

The present invention relates to a culture vessel, and a microscope for observing the sample in the culture vessel.

2. Description of the Related Art

A culture vessel manufactured by disposing a plurality of culture ponds (referred to a well hereinafter) with well-like shapes or concave shapes on a plate (referred to a well plate hereinafter) for cell culture has been known in the art. While a variety of inner diameters of the well are available, the number of the wells disposed on the well plate increases as the inner diameter of the well becomes smaller. A well plate on which wells with an inner diameter of 16.5 mm or less, or 24 or more of the wells, are disposed is practically used (for example, the Multi-well Plate 3047 and Micro-test Plate 3070 made by Becton Dikinson Co. have 24 wells and 96 wells, respectively).

However, the range where a phase contrast effect is obtainable is limited to a central portion of the well when one attempts to observe the cells cultured on a well plate having many wells with a small inner diameter, because the liquid surface of the culture medium in each well is curved due to surface tension of the liquid surface. It is needless to say that this tendency becomes evident as the inner diameter of the well becomes smaller, or the number of the wells becomes larger, being extremely evident in the well plate on which 96 wells are disposed.

The inventor of the present invention has disclosed a method (referred to a related method hereinafter) for solving the foregoing problems in J. P. Preliminary Publication No. Hei 8-5929. In the basic construction of the related method, an attachable and detachable lens system having a positive refractive power is placed between the condenser lens disposed in the illumination optical system of the microscope and well plate as described above so as to cancel the negative refractive power generated by surface tension of the culture medium, thereby spreading the available range for obtaining the phase contrast effect to enable a comfortable phase contrast observation with the microscope.

Although the related example described above is basically worth evaluating, a favorable construction for responding to various conditions should be considered for turning the method to practical uses. One of the conditions to be considered will be described referring to FIG. 1 and FIG. 2. FIG. 1 illustrates the construction in the related example while FIG. 2 is provided for describing the problems in the related example. In FIG. 1, the reference numeral 1 denotes a ring-shaped opening (a diaphragm) disposed in the illumination optical system, the reference numeral 2 denotes a condenser lens, and the reference numeral 3 denotes an attachable and detachable lens system having a positive refractive power placed in the optical path of the illumination optical system. However, the lens system 3 is not necessarily composed of one lens element. The reference numeral 4 denotes a well plate on which a number of wells 5 are disposed. A cultivation medium 6 is filled in each well 5. The reference numerals 7 and 8 correspond to an objective lens and a phase contrast plate, respectively, while the reference numeral 8a denotes a phase contrast membrane.

The construction as described above enables a phase correction when the center line 5-0 of the inner diameter of the well 5 is exactly or nearly exactly aligned with the optical axis 3-0 of the lens system 3. However, when the center line 5-0 of the inner diameter of the well 5 is not aligned with the optical axis 3-0 of the lens system 3 but the lines are considerably separated with each other, a sufficient phase correction becomes difficult.

When the lens system 3 is attached to fix its optical axis to the optical axis of the illumination optical system with a construction not to allow the lens 3 (and its optical axis 3-0) to move in the related example, the center line 5-0 of the well can not be aligned with the optical axis 3-0 of the lens system 3 when the well plate 4 is allowed to move for observing the peripheral region of the well. Consequently, a sufficient phase correction becomes impossible thus making observation of the peripheral region difficult. When the optical axis of the lens system 3 is not fixed to the optical axis of the illumination optical system, on the other hand, the lens system 3 should be moved independently from the movement of the well plate 4 for every wells for successively observing different plural respective wells 5, requiring a considerable time for the movement as well as poor working performance.

Moreover, both of the projection position and projection magnification of the ring-shaped opening are simultaneously corrected by using two or more of lenses for the purpose of expanding the area where a phase contrast effect is obtainable in the related example, using two or more of lenses as described above renders a relatively high production cost as compared with the case that uses single lens with a positive refraction power.

SUMMARY OF THE INVENTION

Accordingly, one object of the present invention is to provide a culture vessel that enables favorable microscopic observation of the sample accommodated in a plurality of wells arranged on a well plate.

Another object of the present invention is to provide a microscope by which phase contrast observation of each sample is facilitated using the culture vessel as described above.

For attaining the foregoing object, the present invention provides in a first aspect a culture vessel provided with a well plate, on which a plurality of concave portions for accommodating a sample are arranged, and a lens array, wherein the lens array is disposed at the opening side of the concave portions by allowing each lens to confront respective concave portions, each lens having a positive refractive power and being arranged to be coaxial with the center line of the confronting concave portion.

In another aspect, the present invention provides a microscope provided with a light source, a condenser lens, an illumination optical system having a ring-shaped opening and an observation optical system capable of observing the sample in the culture vessel, wherein the culture vessel is provided with a well plate, on which a plurality of concave portions for accommodating the sample are arranged, and a lens array, the lens array being disposed at the opening side of the concave portions by allowing each lens to confront respective concave portions, each lens having a positive refractive power and being arranged to be coaxial with the central line of the confronting concave portion. The first ring-shaped opening to be used for observing the sample using the culture vessel, and the second ring-shaped opening to be used for observing the sample without using the culture vessel are disposed to be compatible with each other, the aperture of the first ring-shaped opening being smaller than the aperture of the second ring-shaped opening.

These and other objects as well as the features and the advantages of the present invention will become apparent from the following detailed description of the preferred embodiments when taken in conjunction with the accompanying drawings.

DESCRIPTION OF THE PREFERRED EMBODIMENT

Figure 1:
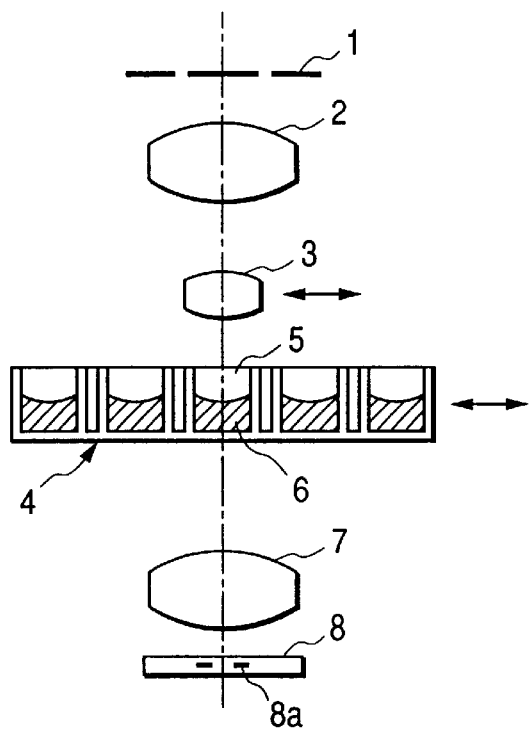
FIG. 1 is a sectional view of an optical system of the conventional microscope also showing the conventional well plate.
Figure 2A:
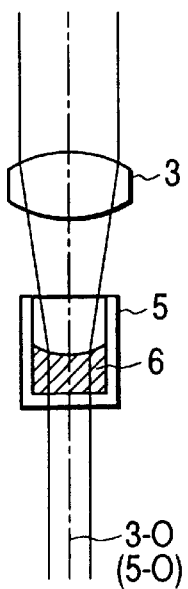
FIG. 2A is a sectional view showing a favorable arrangement of a lens system and a well in the microscope.
Figure 2B:
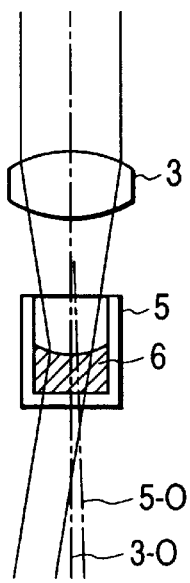
FIG. 2B is a sectional view showing an unfavorable arrangement of a lens system and a well in the microscope.

The culture vessel according to the present invention is composed of a well plate, on which a plurality of wells for accommodating the sample are arranged, and a lens array confronting each well and disposed at the opening side of each well, each lens arranged in the lens array having a positive refractive power, the optical axis of the lens being constructed to be approximately aligned with the center line of the confronting well (being approximately coaxial).

The construction as described above allows each well to be simultaneously moved with the corresponding lens while keeping a coaxial relation with each other when the sample in each well is observed by a microscope (especially by a phase contrast microscope), thereby enabling a sufficient phase contrast effect in observing the periphery of the well. While the center line of each well has been aligned to the optical axis of the lens having a positive refractive power for every observation in the conventional case when inside of each well is to be continuously and successively observed, such need can be excluded in the present invention, largely improving performance of the observation. When the lens array is composed of liquid crystal lenses, the refractive power can be made to be variable, thus enabling to meet various conditions of the culture medium.

The microscope according to the present invention is an inverted phase contrast microscope provided with an illumination optical system having a condenser lens and ring-shaped opening, and an image forming optical system (observation optical system) having an objective lens, which has a favorable construction for observing the sample in the culture vessel with the foregoing arrangement. In other words, the microscope according to the present invention is provided with a first ring-shaped opening to be used for observing the sample using the culture vessel with the foregoing arrangement, and a second ring-shaped opening to be used for observing the sample without using the foregoing culture vessel, the aperture of the first ring-shaped opening being smaller than the aperture of the second ring-shaped opening.

In observing the sample in the culture vessel having the foregoing arrangement with a microscope having a conventional construction, the projection magnification becomes too large by correcting the projection position of the opening, making it impossible to project the opening on the phase contrast film of the phase contrast objective lens. Accordingly, the aperture of the ring-shaped opening to be used for observing the sample using the foregoing culture vessel is made smaller than the aperture of the ring-shaped opening to be used for observing the sample without using the foregoing culture vessel in the microscope according to the present invention, thereby allowing the opening to be projected on the phase contrast film to obtain a sufficient area for the phase contrast effect.

When the well plate and lens array is arranged to be independently attachable and detachable with each other in the illumination optical path in the construction of the culture vessel, a plurality of the well plates can be observed using one lens array by successively replacing the well plates. When the lens array is not inserted in the optical path, on the other hand, an observation of the sample in the culture vessel with a large inner diameter is made possible irrespective of whether the culture vessel is constructed as a well plate or not. Provided that R1 denotes the aperture of the ring-shaped opening to be used when the lens array is inserted into the illumination optical path and R2 denotes the aperture of the ring-shaped opening to be used when the lens array is not inserted into the illumination optical path, then the favorable relation between R1 and R2 is represented by $0.1 < R1/R2 < 0.9$, the relation of $0.25 < R1/R2 < 0.75$ being most favorable.

EMBODIMENT 1

Figure 3:
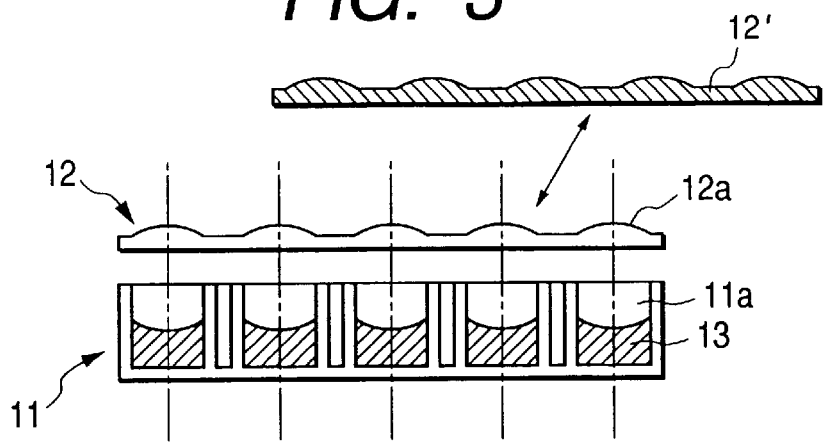
FIG. 3 is a sectional view showing a first embodiment of a culture vessel of the present invention.

In Embodiment 1, the culture vessel is composed of a well plate 11 and a lens array 12 as shown in FIG. 3. A plurality of wells 11a are arranged on the well plates, and a culture medium 13 is filled in each well from circular openings for cultivation of cells.

The lens array 12 is disposed on the opening side of each well 11a, being arranged so as to allow a plurality of lenses 12a to confront the opening of each well 11a. Each of the lenses 12a has a positive refractive power and its optical axis is aligned so as to be approximately coaxial with the center line of the diameter of the respective confronting well 11a. The lens array 12 is made to maintain a relative position to the well plate 11 as shown in FIG. 3 by an appropriate means not shown in the drawing. The lens array 12 can be detached from the well plate 11 for taking the culture medium 13 in and out.

Since the culture vessel according to the present invention has a construction as hitherto described, the well plate 11 and lens array 12 are placed under the microscope with the arrangement shown in FIG. 3, thereby making it possible to cancel the negative refractive power caused by the surface tension of the liquid surface of the culture medium 13 by the positive refractive power of the lens 12a. Since the optical axis of each lens 12a is aligned to be approximately coaxial with the center line of the diameter of the each well 11a, a phase contrast observation of many wells is made possible over a wide area of the well plate 11. Furthermore, it is possible to move the well plate 11 simultaneously with the lens array 12 for successively observing a plurality of wells 11a on the well plate 11, excluding the need of aligning the center line of the diameter of each well 11a with the optical axis of the lens system having a positive refractive power for every observation of the different wells.

When a well plate having 24 to 96 wells 11a with a diameter of each well 11a of 5 to 16.5 mm is used, the expected effect can be obtained by adjusting the focal length of each lens 12a to 10 to 150 mm, a focal length of 20 to 50 mm being most favorable. In the culture vessel according to the present invention, the observation may be continued by replacing the well plate 11 with another well plate while leaving merely the lens array 12 to be set under the microscope after required observations of the wells 11a on the well plate 11 have been completed. To the contrary, the observation also may be performed by replacing the lens array 12 with another lens array 12' (FIG. 3) having a refractive power different from the lens array 12 while using the same well plate 11. While the lens 12a according to the present invention is a plano-convex lens whose flat face is directed toward the well 11a, a plano-convex lens whose convex face is directed toward the well 11a or a biconvex lens may be used. A meniscus lens having a positive refractive power may be also used. Since the liquid surface of the culture medium 13 is not a spherical surface in the strict sense, adjusting the lens surface to be aspherical is effective.

EMBODIMENT 2

Figure 4A:
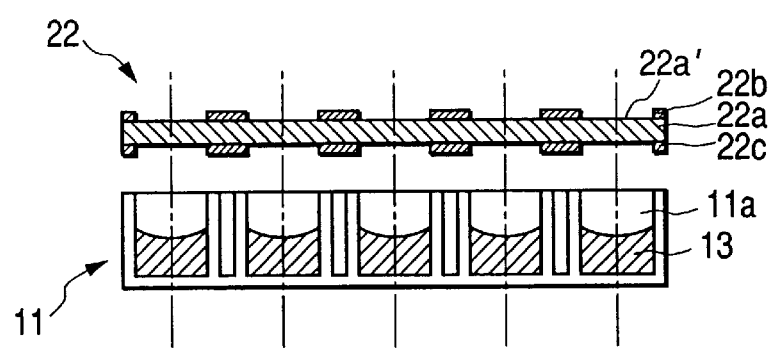
FIG. 4A is a sectional view showing a second embodiment of the culture vessel of the present invention.
Figure 4B:
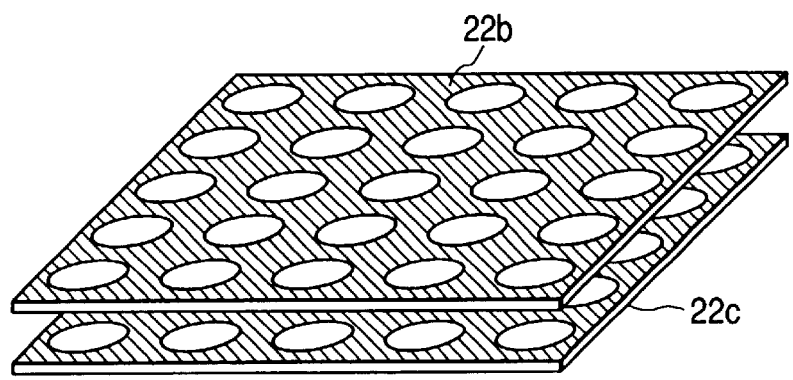
FIG. 4B is a perspective view of two electrodes shown in FIG. 4A.

Embodiment 2 is explained referring to FIG. 4. FIG. 4A denotes a cross section showing the overall construction of the culture vessel according to the present invention while FIG. 4B is perspective views of two electrodes shown in FIG. 4A. The culture vessel according to this embodiment is composed of a well plate 11 and lens array 22. The same reference numerals are attached to the construction of the well plate 11 and culture medium 13 because they are exactly identical to those in Embodiment 1. Accordingly, precise descriptions of them are omitted.

The lens array used in this example is composed of liquid crystal lenses, electrodes 22b and 22c being attached on both faces of the liquid crystal 22a so as to leave a plurality of circular opening regions to serve as respective lenses 22a' behind. The optical axis of each lens 22a' is aligned to be approximately coaxial with the center line of the diameter of each well 11a. The focal distance of each lens 22a' in this lens array 22 is made to be variable in response to the imposed voltage changes to the electrodes 22b and 22c. The liquid crystal lens like this has been reported in The Optical Society of Japan, No. 15, p 49 to 54, published on Feb. 13, 1998. Therefore, precise descriptions of them are omitted.

As known in the art, the negative refractive power generated on the liquid surface of the culture medium 13 is varied depending on the volume and concentration of the culture medium. Accordingly, it is preferable to correct the positive refractive power for optimum cancellation of the negative refractive power. However, the focal distance of each lens 22a' is made variable by changing the imposed voltage in this example, thereby enabling to correct the focal distance so as to obtain an optimum positive refractive power. When only a pair of electrodes 22b and 22c are provided in the liquid crystal lens, the focal length of respective lenses 22a' can be uniformly changed while, when independent electrodes are provided for respective lenses 22a', the focal length can be individually changed.

An observation by replacing merely the well plate 11 with another well plate while allowing the lens array 22 to be set on the microscope as described in Embodiment 1 is possible by constructing the lens array according to this embodiment so that it can be removed from the well plate 11 depending on requirements. The lens array 22 according to this embodiment is more advantageous than the lens array 12 in Embodiment 1 in this case because the positive refractive power can be corrected for every change depending on the conditions of the culture medium in the replaced well plate.

EMBODIMENT 3

Figure 5:
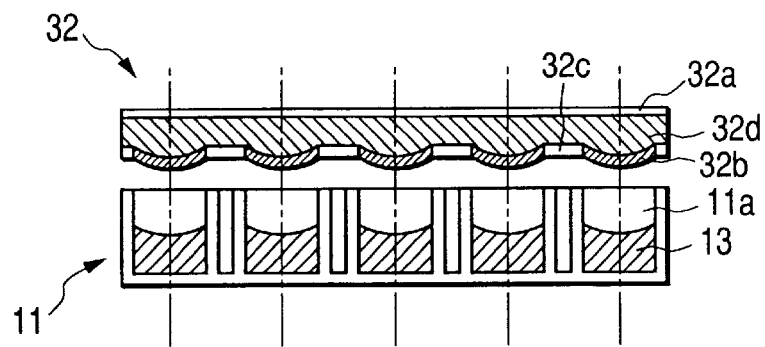
FIG. 5 is a sectional view showing a third embodiment of the culture vessel of the present invention.

Embodiment 3 is explained referring to FIG. 5. FIG. 5 is a cross section showing the overall construction of the culture vessel according to this embodiment, which is composed of a well plate 11 and lens array 32. Of this construction, since the construction of the well plate 11 and the culture medium 13 are the same as those in the foregoing embodiments, the same reference numerals are attached to them and their explanations are omitted. The lens array 32 in this embodiment is composed of liquid lenses, which is constructed of a parallel flat plate 32a, a parallel flat plate 32c on which elastic materials 32b are disposed in the plurality of opening regions to serve as lenses, and a liquid 32d filled between the parallel flat plates 32a and 32c.

Since the lens array 32 according to this embodiment is composed of liquid lenses, the positive refractive power of each lens can be corrected by changing the space between the two parallel flat plates 32a and 32c. In other words, the liquid 32d presses each elastic material 32b when the space between the two parallel flat plates 32a and 32c is narrowed, increasing the positive refractive power. The optical axis of each lens is also made to be coaxial with the center axis of the inner diameter of each well 11a as in other embodiments as hitherto described. Accordingly, although the focal length can not be changed for respective lenses, the other features as described in Embodiment 2 can be also valid in this embodiment.

EMBODIMENT 4

Figure 6:
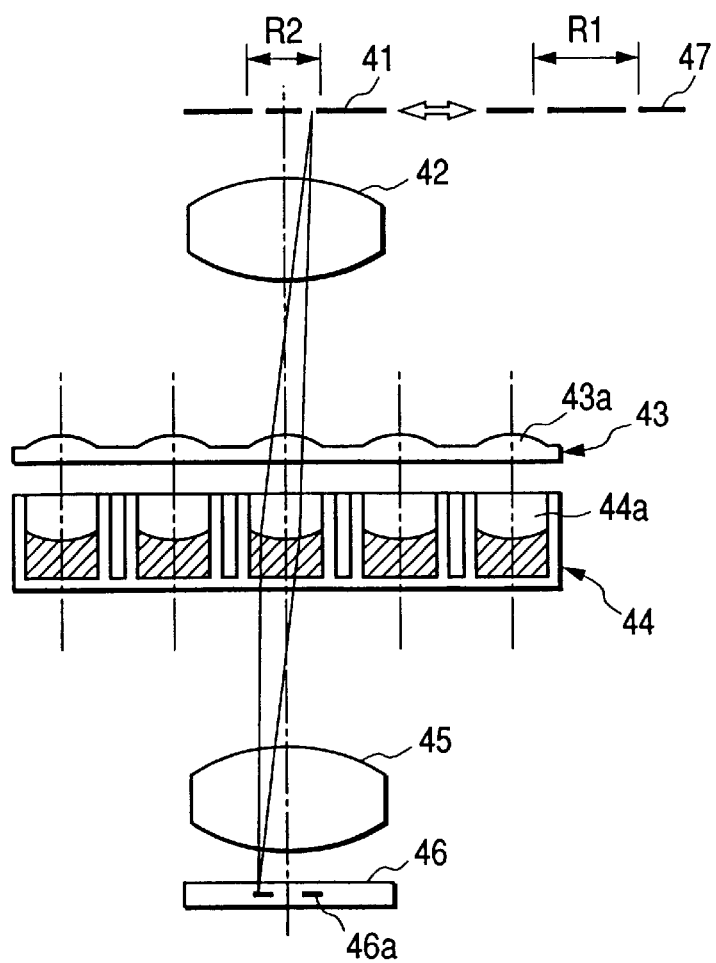
FIG. 6 is a sectional view showing the fourth embodiment of the culture vessel of the present invention also showing a lens system of the microscope.

Embodiment 4 is explained referring to FIG. 6. This embodiment is related to a microscope the construction of which is illustrated in FIG. 6 in a manner similar to FIG. 1 that has been already explained. The microscope according to this embodiment is an inverted phase contrast microscope, in which a ring-shaped opening 41, a condenser lens 42, a lens array 43, a well plate 44, an objective lens 45 and a phase contrast plate 46 are disposed in this order viewed from the light source side, wherein the phase contrast film 46a of the phase contrast plate 46 is disposed to be in conjugated relation with the projection pupil position or projection pupil of the objective lens 45.

It is needless to say that the relative disposition between the lens array 43 and well plate 44 is also adjusted to be approximately coaxial with the center line of each confronting well in this embodiment having the construction as described above. Moreover, since the lens array 43 is separable from the well plate 44, the lens array 43 can be independently attached and detached in the optical path. Accordingly, when only the lens array 43 is mounted in the optical path, different well plates not equipped with the lens array can be inserted into the optical path to observe the inside of each array.

While the projection position of the ring-shaped opening can be corrected by disposing the lens array 43 having a positive refractive power in the construction according to this embodiment, the projection magnification can not be adjusted as in the case not inserting the lens array 43. Therefore, the aperture of the ring-shaped opening 41 in this embodiment is made smaller than the aperture of the ring-shaped opening 47 to be used when the lens array 43 is not inserted into the optical path, thereby correcting the rate of variation of projection magnification to enable projection of the ring-shaped opening 41 onto the phase contrast film 46a.

In this embodiment, the focal distance due to the lens function of the liquid surface in the well 44a is 11.3 mm and the focal length of the lens 43a is 23.9 mm. The projection magnification of the ring-shaped opening 41 when the lens array 43 and well plate 44 are not disposed in the optical path is 0.46 while the projection magnification of the ring-shaped opening 41 when the lens array 43 and well plate 44 are disposed in the optical path is 1.1. The ratio between the aperture R1 of the ring-shaped opening 47 and the aperture R2 of the ring-shaped opening 41 is represented by the relation of R1/R2=0.42.

Although the projection magnification of the ring-shaped opening is varied in response to the change of the negative refractive power ascribed to the inner diameter of the well 44a and the concentration of the culture medium, as well as the change of the distance between the liquid surface of the culture medium and the lens 43a, the projection magnification becomes effective within the range of 0.1<R1/R2<0.9 and becomes optimum within the range of 0.25<R1/R2<0.75. When the ratio is within the range of R1/R2 >0.9, correction of the projection magnification becomes ineffective while a range of 0.1>R1/R2 makes the projection diameter against the change of the projection magnification too small.

The culture vessel and microscope according to the present invention allows a wide area of favorable observation of the sample in the plural wells even when a negative refractive power is generated in the culture medium owing to a small diameter of the opening of the well because the well plate has a number of wells.

What is claimed is:

1. A culture vessel comprising a well plate having a plurality of concave portions for accommodating a sample, and a lens array, wherein said lens array is disposed at the opening side of said concave portions by allowing each lens of said lens array to confront a respective concave portion, said each lens having a positive refractive power and being arranged to have a common axis with the central line of said concave portion.

2. A culture vessel according to claim 1, wherein the refractive power of said each lens is variable.

3. A culture vessel according to claim 2, wherein the refractive power of said each lens is independently variable from the other.

4. A culture vessel according to claim 1, further comprising another lens array having the same arrangement position as said lens array, at least one lens of said another lens array having a different refractive power from said lens array, said two lens arrays being compatible with each other.

5. A culture vessel according to claim 1, wherein each lens of said lens array has a positive refracting power selected to cancel a negative refracting power produced at each of the respective concave portions.

* * * * *